United States Patent [19]

Nitecki et al.

[11] Patent Number: 5,173,482

[45] Date of Patent: Dec. 22, 1992

[54] IMMUNOSUPPRESSIVE ANALOGUES AND DERIVATIVES OF SUCCINYLACETONE

[75] Inventors: Danute E. Nitecki; Margaret Moreland, both of Berkeley; Lois Aldwin, San Mateo; Corey H. Levenson, Oakland; Irwin Braude; David F. Mark, both of Danville; Henry Rapoport, Berkeley, all of Calif.

[73] Assignee: Cetus Corporation, Emeryville, Calif.

[21] Appl. No.: 624,078

[22] Filed: Dec. 6, 1990

Related U.S. Application Data

[62] Division of Ser. No. 434,870, Nov. 13, 1989, abandoned, which is a division of Ser. No. 324,360, Mar. 15, 1989, Pat. No. 4,895,872.

[51] Int. Cl.$^5$ .............................................. A61K 31/66
[52] U.S. Cl. ...................................... 514/125; 514/137
[58] Field of Search ............... 514/557, 574, 554, 137, 514/125

[56] References Cited

U.S. PATENT DOCUMENTS

| | | | |
|---|---|---|---|
| 4,670,467 | 6/1987 | Hess et al. | 514/557 |
| 4,760,090 | 7/1988 | Nissen | 514/557 |
| 4,764,531 | 8/1988 | Nissen | 514/557 |
| 4,835,185 | 5/1989 | Nissen | 514/557 |

OTHER PUBLICATIONS

Tschudy, D., et al., 1982, *Chem. Abstracts*, 96: 210579d.
Weinback, E. C., et al., 1985, *Chem. Abstracts*, 103: 35547f.
Beaumont, C., et al., 1986, *Chem. Abstracts*, 105: 150346t.
Hoult, R. C., et al., 1986, *Chem. Abstracts*, 105: 222421p.
Hamilton, J. W., et al., 1988, *Chem. Abstracts*, 109: 167885y.
Skolik, S. A., et al., 1988, *Chem. Abstracts*, 109: 183224n.

*Primary Examiner*—Frederick E. Waddell
*Assistant Examiner*—Zohreh A. Fay
*Attorney, Agent, or Firm*—Gregory J. Giotta; Wean K. Wong; Albert P. Halluin

[57] ABSTRACT

Succinylacetone derived or related medicaments and methods of synthesis of the same are shown wherein the medicaments consists of succinylacetonyl-proline-PEG, succinylacetonyl-NH-PEG, or compounds that have the formula:

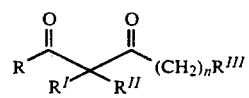

wherein $n = 1-6$

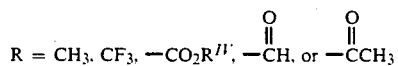
$R = CH_3, CF_3, -CO_2R^{IV}, -CH$, or $-CCH_3$

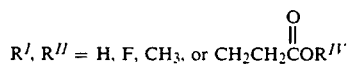
$R^I, R^{II} = H, F, CH_3$, or $CH_2CH_2COR^{IV}$

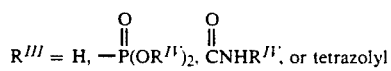
$R^{III} = H, -P(OR^{IV})_2, CNHR^{IV}$, or tetrazolyl $R^{IV} = H$, or alkyl and that have immunosuppressive activity both in vivo and in vitro based on their activities in cellular immunologic assays and adjuvant induced arthritis in rats, respectively.

12 Claims, 7 Drawing Sheets

SUCCINYL ACETONE (SA)

METHYL ESTER-SA

METHYL 4 ACETYL-5-OXOHEXANOATE

FIG.1-2
SA-PRO-NH-PEG(4K) 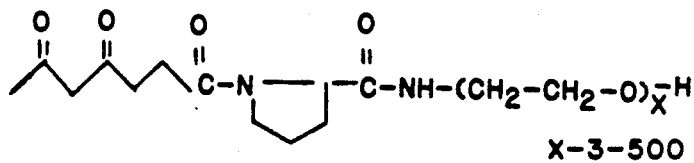
X-3-500
BUTYL SA 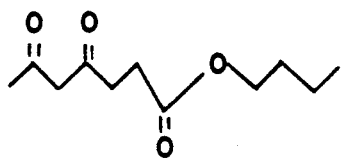
n-OCTYLAMIDE-SA 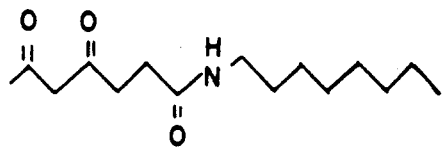
n-BUTYLAMIDE-SA 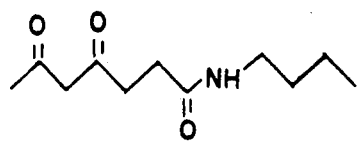
t-BUTYLAMIDE-SA 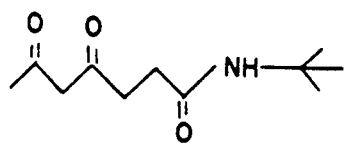
GLUTARYLACETONE METHYL ESTER 
GLUTARYLACETONE (ACID) 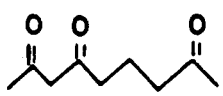
ADIPOYLACETONE METHYL ESTER 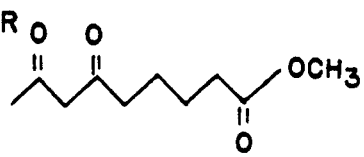

FIG.1-3
SA-HEXYLAMIDE 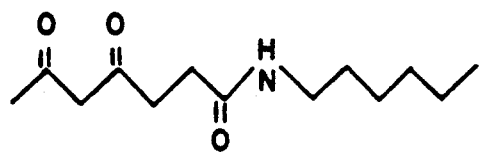
6-HYDROXY-4-OXO HEPTANOIC ACID DERIVATIVE 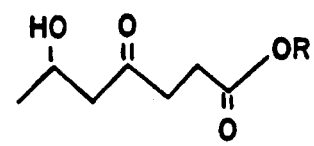
4-HYDROXY-4-OXO HEPTANOIC ACID DERIVATIVES
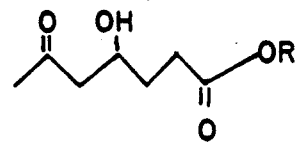
4-6-DIOXO 7,7,7-TRIFLUORO HEPTANOIC ACIDS
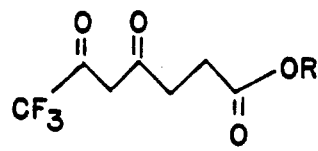
4,6-DIOXO 5,5-DIFLUORO HEPTANOIXC ACID
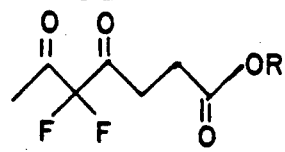
4,6-DIOXO 5,6 5,5-DIMETHYL HEPTANOIC ACID
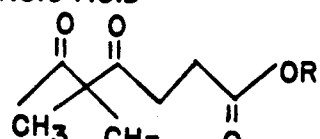
4,6-DIOXOHEXANOIC ACID DERIVATIVES
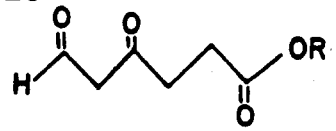
4,6-DIOXOPIMELIC ACID DERIVATIVES
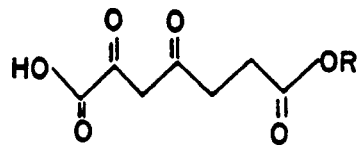

FIG.1-4
4,6,8-TRIOXONONANOIC ACID DERIVATIVES 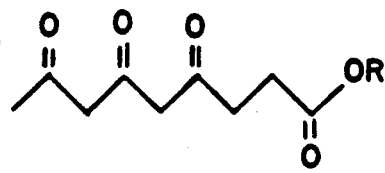
3,5-DIOXOHEXANOIC PHOSPHONISC ACID DERIVATIVES 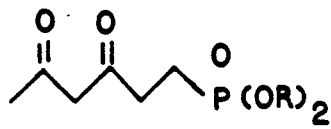
5-(3,5-DIOXOHEXYL) TETRAZOLE 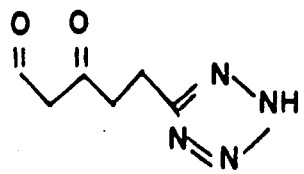
4,6-DIOXOHEPTYL ALCOHOL AND ITS PHOSPHATE ESTER 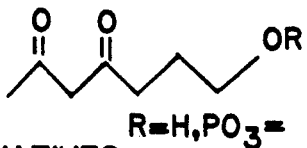
R=H, $PO_3^=$
4,4-DIACETYL PIMELIC ACID DERIVATIVES 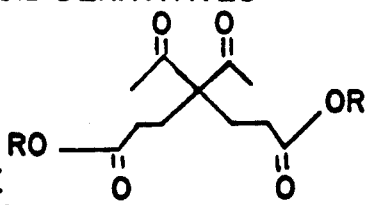
N,N-DIACETYL β-ALANINE 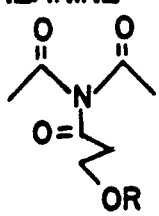

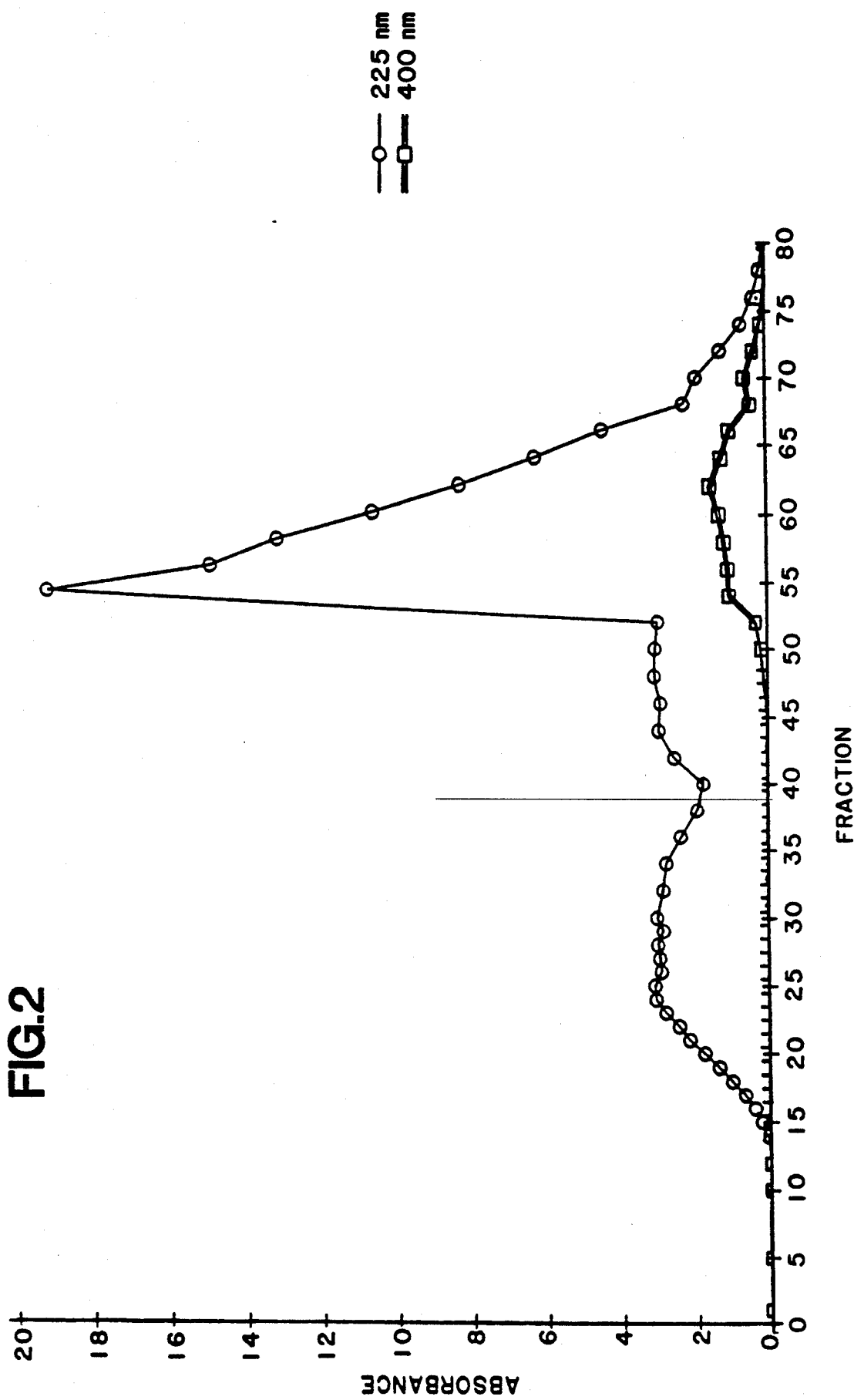

IMMUNOSUPPRESSIVE ANALOGUES AND DERIVATIVES OF SUCCINYLACETONE

This application is a divisional of copending U.S. patent application Ser. No. 434,870, filed Nov. 13, 1989 now abandoned, which is a divisional application of its copending U.S. Ser. No. 324,360, filed Mar. 15, 1989, the latter has been issued as U.S. Pat. No. 4,895,872 on Jan. 23, 1990.

TECHNICAL FIELD OF THE INVENTION

This invention is in the area of immunology, and specifically relates to immunopharmacology as applied to the development of immunosuppressive drugs that are useful in treating a wide variety of diseases arising from a dysfunctional hyperactive immune system. Compositions and methods of using the same that are particularly useful in treating autoimmune diseases are shown.

BACKGROUND OF THE INVENTION

There is a continuous search for therapeutics that have immunosuppressive activity, and therefore facilitate organ tissue transplants, as well as being beneficially applied to the treatment of various autoimmune diseases. The basis of organ tissue rejection is known and resides in the histocompatibility two locus (H-2) in the mouse, and the human leucocyte antigen (HLA) complex in the human. Klein, J., et al. *Ann. Rev. Immunol.* 1:119 (1983). Both systems code for cell surface molecules that are recognized as foreign in a recipient host. Only in those instances where the donor and recipient are genetically identical, that is when the when the donor and recipient are identical twins, is there little or no chance or rejection of the transplanted organ. However, since the donor and recipient are rarely genetically identical, some degree of histocompatibility antigenic mismatch is present, and hence the application of immunosuppressive drugs is required. This is true, even where donors and recipients are HLA matched, that is, matched with the antigens of the major histocompatibility complex loci, since rejection of the transplant can still arise as a result of mismatching of minor genetic loci that are also involved in rejection.

Immunosuppressive drugs are also widely used in the area of graft versus host rejection, particularly bone marrow transplants. The graft from a donor contains a significant number of immunocompetent lymphoid cells that can mount an effective destructive reaction against host cells. Bone marrow transplants are often employed to treat various malignant diseases, including leukemia. Generally this involves immunologically crippling the leukemic patient, and then transplanting bone marrow from a donor. Unless the lymphoid cells in the donor marrow are suppressed they can react against recipient tissue antigens, often with dire consequences.

A variety of drugs, and antisera to lymphoid cells are used as immunosuppressives. Particularly useful drugs are corticosteroids, othiopirne, and cyclosporin. In addition, various monoclonal antibodies, alone or when coupled to a cytotoxic agent are available for ridding the donor marrow of lymphoid cells. P. S. Russell et al., *Annual Review Medicine* 35:63 (1984). In addition, U.S. Pat. No. 4,670,467 claims succinylacetone (SA, 4,6-dioxoheptanoic acid) as an immunosuppressive medicament. Succinylacetone is a seven carbon organic ketoacid.

In addition to being used in the area of organ tissue transplantation, and graft versus host disease, immunosuppressive drugs are widely sought after to treat autoimmune diseases. Autoimmunity can generally be defined (Smith, H. and Steinberg, A. Autoimmunity—A perspective *Ann. Rev. Immunol.* 1:175 (1983)) as the generation of an immune response against a person'own self components. Autoimmune diseases generally develop spontaneously in humans. Both a person's genetic predisposition, as well as environmental factors may play a role. Those agents which are thought to initiate autoimmunity are poorly defined. However, autoimmunity can be induced in experimental animals by suitable immunization procedures with known antigens. Classical examples of experimentally induced autoimmune diseases in animals are experimental or allergic encephalomyelitis, and adjuvant induced arthritis. The former is induced by immunization with a myelin basic protein, and induces an autoimmune disease having neurological symptoms involving partial or complete paralysis of the hind legs of animals. The latter entails use of any microbacterium for induction of arthritis in rats. Examples of autoimmune diseases in humans include various forms of diabetes systemic lupus erythematosus, myasthenia gravis, chronic thyroiditis, hemolytic anemia, and multiple sclerosis. Additionally, rheumatoid arthritis is often considered an autoimmune disease.

Many autoimmune diseases are through to occur by different immune mechanisms. This includes a cytotoxic mechanism whereby antibody reacts with antigen, and the resulting complex becomes membrane associated. Often this initiates complement mediated lysis of the involved cells. A second mechanism involves the interaction of lymphoid cells, rather than antibodies and complement, with antigen. Often this results in an inflammatory response, such as that seen in rheumatoid arthritis.

Immunosuppressive drugs are used to treat autoimmune diseases, much as they are used to treat organ tissue transplants and graft versus host disease. In the clinical arena, cyclosporin A has been shown to be effective in treating various experimentally induced autoimmune diseases. Shevach, E. *Ann. Rev. Immunol.* 3:397 (1985). These include experimental allergic encephalomyelitis, and an autoimmune form of diabetes which develops in the BB rat strain. Similarly, cyclosporin A has been applied in the clinical setting, and used to treat patients with posterior uveitis. Similarly, it has been used to treat type-1 diabetes mellitus in humans. Despite these results, however, cyclosporin A has side effects which has limited its use in the clinical setting. In addition to cyclosporin A, other immunosuppressive drugs have been shown to have a degree of efficacy when used to treat various autoimmune disease. For example, corticosteroids are often used to treat rheumatoid arthritis. Hereto, however, corticosteroids are by no means a cure, but rather provide temporary relief, all-be-it with severe toxic side effects.

SUMMARY OF THE INVENTION

An object of the invention is to provide immunosuppressive compounds that are useful in treating patients suffering from diseases associated with hyperactive immune systems.

Another object of the invention is to provide analogues or derivatives of succinylacetone that have hithertofore unknown immunosuppressive activity when applied to the treatment of graft versus host disease, or autoimmune diseases.

A third object of the invention is to provide derivatives of succinylacetone that are maintained in a patient's circulation for longer times than succinylacetone.

A fourth object of the invention is the description of immunosuppressive compounds that have the formula:

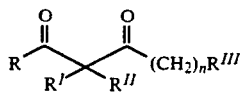

wherein n = 1-6

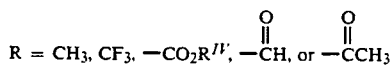

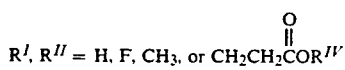

$R^{IV}$ = H, or alkyl

A further object of the instant invention is to describe methods whereby derivatives of succinylacetone can be administered to patients in effective amounts to control or eliminate graft host disease or various autoimmune diseases.

Other objects and advantages of the present invention will become apparent upon a reading of the detailed description below.

BRIEF DESCRIPTION OF THE TABLES

Table 1 presents data showing the effects of succinylacetonyl-proline derivatized polyethylene glycol 4000 on IL-2 and IFN-γ production, as well as the incorporation of triated thymidine into human lymphocytes.

Table 2 shows the effect of succinylacetonyl-proline derivatized with polyethylene glycol 4000 in a phytohemagglutinin assay.

Table 3 shows the effect of succinylacetone methylester on the production of IL-2 and IFN-γ, and the incorporation of tritiated thymidine in a mixed lymphocyte reaction.

Table 4 shows the effect of methyl 4-acetyl-5-oxohexanoate on the production of IL-2 and IFN-γ, and the 13 human lymphoid cells in a mixed lymphocyte reaction.

Table 5 shows the effect of succinylacetone methyl ester and methyl 4 acetyl-5-oxohexanoate in a phytohemagglutinin assay.

Table 6 shows the effect of succinylacetone methyl ester on the incorporation of tritiated thymidine by human lymphoid cells in a secondary mixed lymphocyte reaction.

Table 7 shows the effect of methyl 4-acetyl-5-oxohexanoate on the incorporation of triated thymidine by human lymphoid cells in a secondary mixed lymphocyte reaction.

Table 8 shows the effect of succinylacetone methyl ester on the viability of peripheral blood lymphocytes, with, or without stimulation by phytohemagglutinin.

Table 9 shows the effect of methyl 4-acetyl-5-oxohexanoate on the viability of peripheral blood lymphocytes, with, or without stimulation of phytohemagglutinin.

Table 10 shows the effects of succinylacetone and derivatives in a adjuvant induced arthritis animal model system.

FIG. 2 shows the Sephadex G-50 chromatographic separation of succinylacetonyl-proline-PEG.

DESCRIPTION OF THE INVENTION

The present invention describes several novel immunosuppressive molecules that are analogues or derivatives of succinylacetone (SA).

Most of the compounds can be described by the following formula:

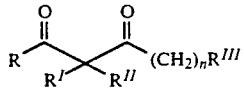

wherein n = 1-6

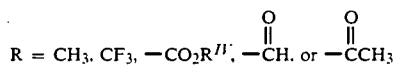

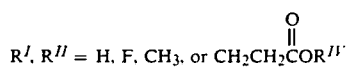

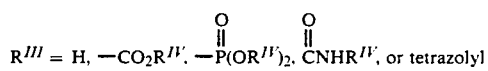

$R^{IV}$ = H, or alkyl

Specific examples of preferred embodiments of the subject immunosuppressive compounds are shown in FIG. I, along with the structure of succinylacetone.

FIG. 1

Succinyl Acetone (SA)

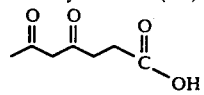

Methyl ester-SA

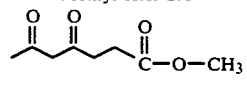

Methyl 4 acetyl-5-oxohexanoate

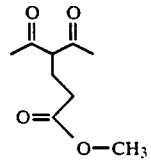

SA-pro-NH-PEG(4K)

Figure 1:
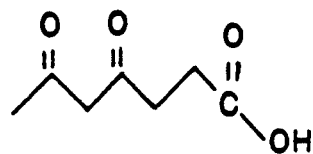
FIG. 1 shows analogues and derivatives of succinylacetone.
Figure 1:
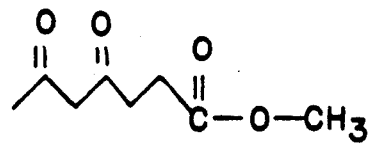
Figure 1:
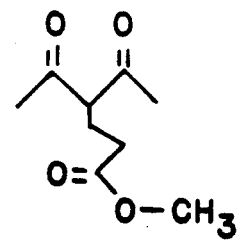

-continued
FIG. 1

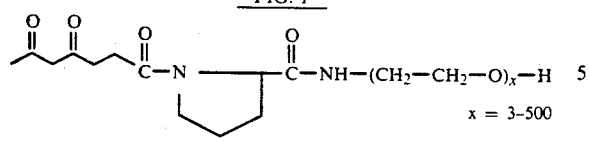
x = 3-500

Butyl SA
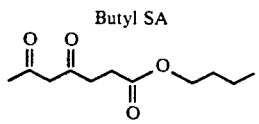

n-octylamide-SA
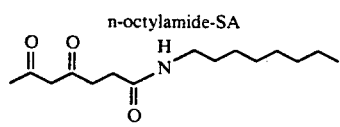

n-butylamide-SA
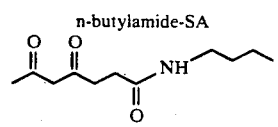

t-butylamide-SA
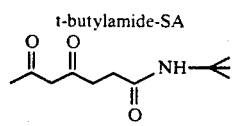

glutarylacteone methyl ester
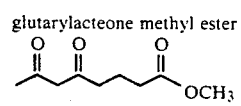

glutarylacetone (acid)
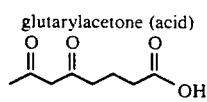

adipoylacetone methyl ester
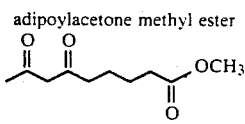

SA-hexylamide
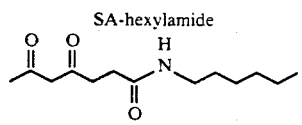

6-hydroxy-4-oxo heptanoic acid derivative
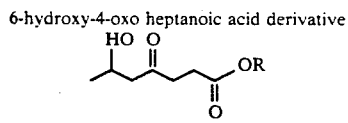

4-hydroxy-4-oxo heptanoic acid derivatives
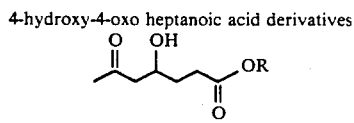

4-6-dioxo 7,7,7-trifluoro heptanoic acids
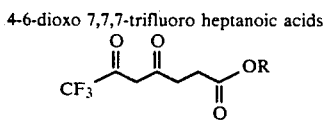

4,6-dioxo 5,5-difluoro heptanoic acid
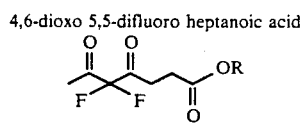

-continued
FIG. 1

4,6-dioxo 5,5-dimethyl heptanoic acid
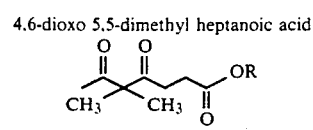

4,6-dioxohexanoic acid derivatives
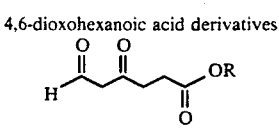

4,6-dioxopimelic acid derivatives
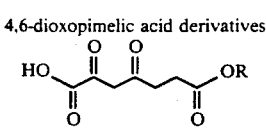

4,6,8-trioxononanoic acid derivatives
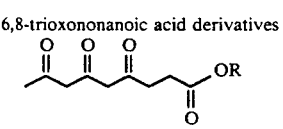

3,5-dioxohexanoic phosphonic acid derivatives
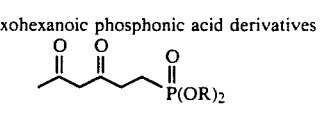

5-(3,5-dioxohexyl) tetrazole
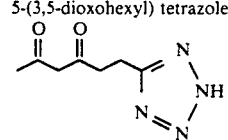

4,6-dioxoheptyl alcohol and its phosphate ester
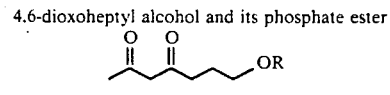

R = H, PO$_3$=

4,4-diacetyl pimelic acid derivatives
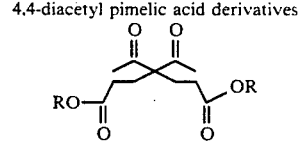

N,N-diacetyl β-alanine
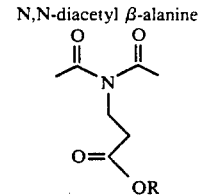

The immunosuppressive properties of the instant molecules can be described both as to in vitro and in vivo efficacy in experimental systems. It is important to point out that the results obtained from the in vitro systems are directly predictive of the in vivo immunosuppressive properties of the derivatives of succinylacetone described herein. The in vitro mixed lymphocyte assay described below is presently employed in the clinical setting as an indicator of histocompatibility, and is premised on the transformation of resting genetically dissimilar lymphocytes into cells which synthesize DNA and undergo proliferation. It has been demonstrated that incompatibility at the major histocompatibility complex is mainly responsible for this phenomenon.

A second assay widely used to study immune responsiveness is mitogenic stimulation of thymocytes with antigenic substances of plant origin. The most widely used plant molecule is phytohemagglutinin (PHA). Although PHA stimulates DNA synthesis nonspecifically in a large number of lymphocytes, unlike true antigenic stimulation which causes mitogenesis of sub-populations of lymphocytes, the susceptibility of a patient's lymphocytes to PHA stimulation has been shown to correlate with the overall immune responsiveness of the patient.

Thus, it will be appreciated as to both the mixed lymphocyte and PHA assay that they are valuable for identifying immune suppressive molecules in vitro, and that the results obtained therefrom are predictive of their in vivo effectiveness.

The following definitions will assist in understanding the invention.

Derivatives of succinylacetone, in addition to those shown in FIG. 1, may include succinylacetone conjugated to polyethylene glycol (PEG), polypropylene glycol (PPG) or other polymer molecules known to extend the in vivo circulation time of medicaments.

The polymer need not have any particular molecular weight, but it is preferred that the molecular weight be between about 300 and 100,000, more preferably between 350 and 40,000, depending, for example, on the particular succinylacetone derivative.

Preferably the PEG homopolymer is unsubstituted, but in may also be substituted at one end with an alkyl group. Preferably the alkyl group is a $C_1$-$C_4$ alkyl group, and most preferably a methyl group. Most preferably, the polymer is an unsubstituted homopolymer of PEG, a monomethyl-substituted homopolymer of PEG or polyoxyethylated glycerol, and has a molecular weight of about 250 to 40,000.

Pegylated proline succinylacetone (succinylacetonyl-proline-PEG) is preferred in the invention and has the structure:

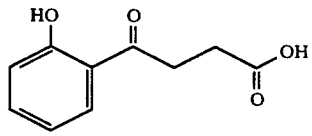

Succinylacetonyl-proline-PEG, the methyl ester derivative, and glutarylacetone, and adipoylacetone, were synthesized as described in detail below. Methyl 4 acetyl-5-oxohexanoate was purchased from Aldrich Chemical Corp. The synthesis of

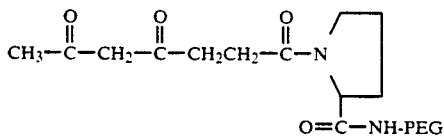

is described in *Journal of Labelled Compounds and Radiopharmacetuicals*, 1985, 22(9):869–881, and in U.S. Pat. No. 4,011,321.

The synthesis of

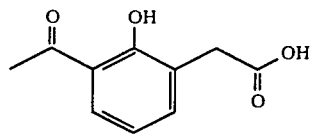

and 4,4-diacetyl pimelic acid are described in Japanese Patent No. 57/203030, and in *Australian Journal of Chemistry*, 1967, 20:123–130, respectively.

Also, N, N-diacetyl β-alanine and 6-hydroxy 4-keto heptanoic acid methyl ester are described in the *Journal of Medicinal Chemistry*, 1985, 28:9–12 and in *Journal of Organic Chemistry*, 1988, 53:4893, respectively. All of the above publications are hereby incorporated by reference in their entireties.

Furthermore, the following compounds may be synthesized as described below:

Succinyl Trifluoroacetone Methyl Ester
Succinyl Trifluoroacetone
Acetoacetonyl Methyl Benzoate
2-Acetoacetonyl Benzoic Acid
Synthesis of 3,5-Dioxohexylacyanide
Synthesis of 5-(3,5-Dioxohexyl) Tetrazole
Synthesis of Beta-Keto t-Butyldimethylsilyl Enol Esters of SA Methyl Ester
Synthesis of Beta-Keto Isopropyl Enol Esters of SA Methyl Ester
Synthesis of Beta-Hydroxy Keto Derivatives of SA Methyl Ester
Synthesis of 4,6,8-Trioxo Methyl Nonanoate Derivatives of succinylacetone were tested for immunosuppressive activity in several different types of assay systems. The first consisted of measuring the amounts of interleukin-2 (IL-2), and interferon-γ (IFN-γ) produced by human lymphoid cells in a mixed lymphocyte reaction. Low levels of these molecules in the reaction mixture indicate that the immune system is being suppressed by the subject succinylacetone derivatives.

IL-2 and IFN-γ levels were determined as follows:

IL-2 was measured by enumerating the number of viable HT-2 cells found after an 18–24 hours period. HT-2 cells are a mouse IL-2 dependent cell line which die in the absence of IL-2. The assay is described by Gillis et al., *J. of Immunol.* 120:2027 (1978).

IFN-γ was determined by measuring the amount of protection conveyed on human WISH cells against the cytopathic effects of encephatomyocarditis virus (EMC). This assay is described by I. A. Bruade, *J. of Immunol. Methods* 63:237 (1983). Both publications are hereby incorporated by reference.

The mixed lymphocyte reaction assay can be carried out by techniques well known to those skilled in the art. L. Hudson and F. C. Huy, *Practical Immunology*, p. 260, Blackwell Scientific Publications (1976). Briefly this consists of isolating lymphocytes from human peripheral blood by standard density gradient centrifugation techniques from two separate individuals. Approximately $2 \times 10^5$ lymphocytes of each individual are combined to yield a total of $4 \times 10^5$ lymphocytes per culture. All procedures are carried out under sterile conditions, and the lymphocytes are isolated and kept in physiologically compatible solutions. To the mixture of lymphocytes is added a desired amount of an appropriate succinylacetone derivative, and after different times an aliquot of the mixture is removed and assayed for IL-2 or IFN-γ, or $^3$H-T is measured.

Succinylacetonyl-Proline-NH-PEG

Table 1 shows that there is a considerable diminution in the amount of IL-2 and IFN-γ produced as a function of the concentration of succinylacetonyl-proline-NH-PEG. It is worth noting that when compared to cell culture media, Roswell Park Memorial Institute media (RPM), not containing succinylacetonyl-proline-NH-PEG, that there is more than about a three fold decrease in the amount of either IL-2, or IFN-γ. It will be appreciated that Table 1 presents the results from two separate experiments.

Table 1 also presents a control experiment wherein the effects of PEG-4,000-NH₂ on IL-2 and IFN-γ production is shown. Although PEG-4000-NH₂ does inhibit the production of these molecules, inhibition, however, is well below that observed for succinylacetonyl-proline-NH-PEG.

As mentioned above, one measure of an immune response as reflected in a mixed lymphocyte assay is the stimulation of DNA synthesis, and a concomitant increase in cell number. Thus, to further ascertain the immunosuppressive activity of succinylacetonyl-proline-NH-PEG, its effect on inhibition of thymocyte growth, as detected by uptake of tritiated thymidine, was assayed. Table 1 shows the results. A 50% reduction in thymidine uptake is observed at a concentration of about 625 μM succinylacetonyl-proline-PEG. This inhibition should be compared to about 2% observed for PEG-4000-NH₂.

isolated from a second individual were tested, it is apparent that the level of inhibition is even greater. Approximately 95% inhibition is observed at a concentration of 8.3 mM succinylacetonyl-proline-NH-PEG, and this diminishes to 38.7% at a concentration of 925 μM.

TABLE II

Succinylacetonyl-proline-NH-PEG-4000 in pHA Assay

| SAMPLE | CPMI ± SD | | % Inhib. | CPMI ± SD | | % Inhib. |
|---|---|---|---|---|---|---|
| 8.3 mM | 8386 | 1242 | (83.6) | 2748 | 786 | (95.2) |
| 2.8 mM | 35839 | 2352 | (29.9) | 23869 | 1410 | (59.0) |
| 925 μM | 45744 | 1129 | (10.6) | 35678 | 12393 | (38.7) |
| 309 μM | 49754 | 4294 | | 47690 | 9003 | (7.2) |
| 102 μM | 49805 | 12018 | | 40562 | 9677 | |
| 34 μM | 51149 | 6031 | | 30116 | 720 | |
| 11.3 μM | 50680 | 2000 | | 34898 | 3607 | |
| RPMI MEDIA | 51149 | 5542 | | 58159 | 4858 | |
| PHA + | 47165 | 1524 | | 51378 | 8890 | |
| PHA − | 126 | 56 | | 135 | 64 | |

Succinylacetone Methyl Ester

A second derivative of succinylacetone which was shown to have considerable immunosuppressive activity is succinylacetone methyl ester. Table 3 shows the effects of varying the concentration of succinylacetone methyl ester on the production of IL-2 or IFN-γ in a mixed lymphocyte reaction. The results from duplicate experiments are shown. The concentration of succiny-

TABLE I

Succinylacetonyl-proline-HH-PEG vs PEG-4000-NH₂

| | IL-2 | | IFN-γ | | CPM (% INHIBITION) | | | |
|---|---|---|---|---|---|---|---|---|
| | | Exp. II | | Exp. II | Exp. I | | EXP. II | |
| SAMPLE | Exp. I | cpm | Exp. I | cpm | cpm | % Inhib. | cpm | % Inhib. |
| SA-pro-NH-PEG | | | | | | | | |
| 10 mM | <7 | <6 | <945 | <1125 | 26 | 99.95 | 127 | 99.7 |
| 5.0 mM | <7 | <6 | <945 | <1125 | 1162 | 97.9 | 182 | 99.6 |
| 2.5 mM | <7 | <6 | <945 | <1125 | 598 | 98.9 | 1467 | 96.9 |
| 1.25 mM | <7 | <6 | 4980 | <1125 | 9729 | 82.7 | 8787 | 81.3 |
| 625 mM | <7 | <6 | 5603 | 1041 | 31490 | 38.5 | 25471 | 45.8 |
| 313 mM | <7 | <6 | 4150 | 2802 | 41599 | 18.8 | 34570 | 26.5 |
| 156 mM | 8 | 8 | 4980 | 2179 | 44129 | 21.7 | 29907 | 36.4 |
| mM | <7 | 5 | 5603 | 2179 | 47326 | 16.0 | 33977 | 27.7 |
| RPMI media | 24 | 19 | 2802 | 1868 | 56358 | — | 47016 | — |
| PEG-4000-NH₂ | | | | | | | | |
| 10 mM | 8 | 10 | 1972 | 1556 | 18545 | 70.7 | 23733 | 43.1 |
| 5.0 mM | 10 | 10 | 3113 | 1868 | 32003 | 49.5 | 28961 | 30.5 |
| 2.5 mM | 15 | 17 | 3113 | 1868 | 50295 | 20.6 | 33330 | 20.1 |
| 1.25 mM | 14 | 17 | 3424 | 1972 | 56850 | 10.2 | 45587 | 9.3 |
| 625 μM | 19 | 17 | 3113 | 1868 | 59571 | 5.9 | 42578 | 2.1 |
| 313 μM | 20 | 26 | 5188 | 1868 | 56774 | 10.3 | 42970 | 3.1 |
| 156 μM | 21 | 41 | 4047 | 1547 | 67188 | 6.1 | 36185 | 13.2 |
| 78 μM | 18 | 23 | 3424 | 1688 | 61969 | 2.1 | 47187 | −13.2 |
| RPMI media | 18 | 25 | 1972 | 1778 | 63327 | — | 41694 | — |

Table 2 shows the effect of succinylacetonyl-proline-NH-PEG in a phytohaemagglutinin assay. The procedure for carrying out the phytohaemagglutinin assay is also well known to those skilled in the art. Briefly, it consists of isolating human lymphocytes as described above, and incubating about $1.0 \times 10^6$ cells per ml in a suitable physiological solution with phytohaemagglutinin, and the appropriate concentration of succinylacetone-proline-NH-PEG. Tritiated thymidine is added 48 hours later and allowed to incubate for twenty-four hours before the cells are counted. Table 2 shows that there is more than an 80% inhibition of tritiated thymidine uptake at a concentration of 8.3 mM, and that this inhibition decreases rapidly to about 10% at a concentration of 925 μM. In a second phytohemagglutinin assay, also shown in Table 2, wherein lymphocytes lacetone methyl ester than inhibits the production of both of these substances by about 50% is 733 μM.

Table 3 also shows the inhibition of tritiated thymidine uptake in a primary mixed lymphocyte reaction as a function of succinylacetone methyl ester concentration. Duplicate experiments are also shown. The concentration that inhibits tritiated thymidine uptake by one-half is approximately 733 μM. Succinylacetone methyl ester was also tested in a phytohaemagglutination assay to further determine the potency of it immunosuppressive activity, and to ascertain whether this assay correlates with the results obtained in the primary mixed lymphocyte reaction assay. Table 5 shows two mixed lymphocyte assays conducted in duplicate using the lymphoid cells from two individuals. The amount of succinylacetone methyl ester that displays a 50% inhibition of phytohaemagglutination stimulation is between 103-309 μM in one assay, and about 103 μM in the second assay.

TABLE III

| | Methyl Ester SA-1° MLR | | | | | | | |
|---|---|---|---|---|---|---|---|---|
| | IL-2 | | IFN-γ | | CPM ± SD | | | |
| SAMPLE | Exp I | Exp II | Exp I | Exp II | Exp I | | Exp II | |
| 20 mM | <6 | <8 | <630 | <375 | 164 | 28 | 90 | 38 |
| 6.7 mM | <6 | <8 | <630 | <375 | 89 | 16 | 126 | 2 |
| 2.2 mM | <6 | <8 | 788 | <375 | 3185 | 486 | 33497 | |
| 733 μM | 14 | 23 | 1890 | 688 | 30535 | 3068 | 40700 | 10026 |
| 244 μM | 19 | 28 | 1575 | 938 | 66159 | 2795 | 78306 | 7352 |
| 81 μM | 24 | 28 | 1628 | 1094 | 80182 | 9420 | 87595 | 1161 |
| 27 μM | 25 | 34 | 2713 | 1032 | 75211 | 2332 | 97879 | 1123 |
| 9 μM | 28 | 38 | 1860 | 1000 | 87101 | 7114 | 110425 | 4941 |
| 3 μM | 41 | 34 | 2558 | 1313 | 81740 | | 114428 | 1060 |
| RPMI | 30 | 54 | 2325 | 1313 | 84707 | 299 | 109628 | 9886 |

Methyl 4 Acetyl-5-Oxohexanoate

An analogue of succinylacetone was shown to have immunosuppressive activity, and this is methyl 4-acetyl-5-oxohexanoate. Table 4 summarizes its immunosuppressive effects in a primary mixed lymphocyte reaction assay where the parameters measured were IL-2 or IFN-γ production. Approximately 2.2 mM methyl 4 acetyl-5-oxohexanoate causes a 50% reduction in the production of either of these molecules. Table 4 also shows the effects of these compounds on the incorporation of tritiated thymidine in a mixed lymphocyte assay. Again, it was observed that the concentration of methyl 4-acetyl-5-oxohexanoate that causes a 50% inhibition in thymidine uptake is about 2.2 mM.

TABLE IV

| | Methyl 4-Acetyl-5-Oxohexanoate-1 MLR | | | | | | | |
|---|---|---|---|---|---|---|---|---|
| Sample | Exp I | Exp II | Exp I | Exp II | Exp I | | Exp II | |
| 20 mM | <6 | <12 | <285 | <469 | 163 | 2 | 109 | 3 |
| 6.7 mM | <6 | <12 | <285 | <469 | 135 | | 21280 | 2448 |
| 2.2 mM | 9 | 35 | 285 | 703 | 29389 | 2138 | 84363 | 4217 |
| 733 μM | 17 | 70 | 570 | 1172 | 67787 | 3233 | 113732 | 5345 |
| 244 μM | 17 | 52 | 998 | 1953 | 48284 | — | 122672 | 21280 |
| 81 μM | 42 | 70 | 1313 | 1560 | 81881 | 2876 | 113054 | 3782 |
| 27 μM | 30 | 52 | 1260 | 1248 | 77634 | 8627 | 112463 | 7009 |
| 9 μM | 46 | 85 | 1260 | 1248 | 77627 | 6627 | 117109 | 3074 |
| 3 μM | 29 | 70 | 1260 | 1144 | 74259 | 4938 | 114713 | 2136 |
| RPMI MEDIA | 23 | 77 | 1260 | 1248 | 77397 | 81 | 114230 | 1186 |

Methyl 4-acetyl-5-oxohexanoate was also tested in a phytohemagglutination assay, and these results are shown in Table 5. Two assays were conducted using lymphoid cells from two individuals. In both assays the concentration of methyl 4-acetyl-5-oxohexanoate that caused about a 50% inhibition in phytohaemagglutination stimulation was about 309 μM.

TABLE V

| PHA - Stimulation of Succinylacetone Methyl Ester And Methyl 4-Acetyl-5-Oxohexanoate | | | | | | | | | |
|---|---|---|---|---|---|---|---|---|---|
| Succinyl-Acetone Methyl Ester | EXP. II | | EXP. II | | Methyl 4 Acetyl-5-Oxohexa-noate | EXP. I | | EXP. II | |
| | cpm | ± SD | cpm | ± SD | | cpm | ± SD | cpm | ±SD |
| 25 mM | 113 | 20 | 112 | 33 | 25 mM | 200 | 108 | 200 | 55 |
| 83 mM | 79 | 29 | 107 | 53 | 83 mM | 192 | 33 | 156 | 28 |
| 2.8 mM | 126 | 38 | 65 | 12 | 2.8 mM | 116 | 41 | 717 | 91 |
| 926 μM | 565 | 36 | 6949,234, 12 | 431 | 926 μM | 2276 | 154 | 5600 | 1195 |
| 309 μM | 5927 | 124 | 5292 | 891 | 309 μM | 14098 | 92 | 19713 | 3109 |
| 103 μM | 17595 | 2625 | 17733 | 6322 | 103 μM | 18677 | 1409 | 30569 | 3168 |
| 34 μM | 16549 | 1394 | 28614 | 5959 | 34 μM | 19399 | 547 | 34006 | 1101 |
| 11 μM | 18100 | 862 | 28645 | 4692 | 11 μM | 19401 | 1995 | 33417 | 7177 |
| 3.8 μM | 20292 | 1643 | 37936 | 2487 | 3.8 μM | 19888 | 3900 | 33799 | 1633 |
| RPMI MEDIA | 21587 | 89 | 36957 | 3908 | | 18405 | 1777 | 38185 | 6925 |

Secondary Mixed Lymphocyte Assays

In addition to testing the immunosuppressive activities of succinylacetone derivatives in a primary mixed lymphocyte reaction, or a phytohemagglutinin stimulation assay, two of the derivatives, succinylacetone methyl ester and methyl 4-acetyl-5-oxohexanoate, were tested in a secondary mixed lymphocyte reaction assay. The secondary mixed lymphocyte assays differs from the primary mixed lymphocyte reaction assays in that they employ many more primed responder cells that are responsive to the primary stimulating cells. The presence of such responsive cells is a reflection of immunological memory in an ongoing immunological response. The protocol for carrying out a secondary mixed lymphocyte assay involves performing a primary lymphocyte assay as described above, and recovering viable cells about 9-10 days after the primary mixed lymphocyte reaction exhibits little or no cell proliferation. Generally between 10% to 50% of the original input cells are recovered in viable condition. These cells are then used in the secondary mixed lymphocyte reaction. It is worth noting that because a secondary mixed lymphocyte reaction is greatly enriched for responsive cells, fewer cells can be used in the secondary assay.

The procedure for carrying out a secondary mixed lymphocyte reaction is described by T. Meoen, *Immunological Methods*, Eds I. Lefkoivits and B. Pernis, Economic Press, New York (1979). It will be appreciated that described therein is a method for carrying out secondary lymphocyte reactions using mouse cells, however such methods are generally applicable to performing secondary mixed lymphocyte reactions using human cells with modifications that are well known to those skilled in the art. Tables 7 and 8 show immunosuppressive effects of succinylacetone methyl ester, and methyl 4-acetyl-5-oxohexanoate on the uptake of tritiated thymidine in secondary mixed lymphocyte assay. The assays were conducted in duplicate involving lymphoid cells isolated from two individuals. It is important to note that the immunosuppressive effects of both chemicals are similar to those observed in the primary mixed lymphocyte reaction assay, and therefore are correlative of their suppressive effects described in that system. For succinylacetone methyl ester or methyl 4-acetyl-5-oxohexanoate the concentration that causes about a 50% reduction in tritiated thymidine uptake is between about 2.2 mM and 740 μM.

TABLE VI

Succinylacetone Methyl Ester 2°-MLR

| Sample | Exp I | | | Exp II | | |
|---|---|---|---|---|---|---|
| | CPM | ± SD | % Inhib. | CPM | ± SD | % inhib. |
| 20 mM | 64 | 29 | (99.9) | 87 | 13 | (99.9) |
| 6.7 mM | 51 | 18 | (9.99) | 62 | 4 | (9.99) |
| 2.2 mM | 11778 | 2205 | (85.4) | 29851 | 6242 | (68.0) |
| 740 μM | 67456 | — | (16.3) | 85447 | 12061 | (8.5) |
| 247 μM | 87337 | 479 | | 125345 | 35225 | |
| MEDIA | 80578 | 8523 | | 93241 | 9086 | |
| PBL | 11658 | 122 | | 50760 | 1581 | |
| EBV | 196 | 35 | | 153 | 62 | |

TABLE VII

Methyl 4-Acetyl-5-Oxohexanoate 2°-MLR

| Sample | Exp I | | | Exp II | | |
|---|---|---|---|---|---|---|
| | CPM | ± SD | % Inhib. | CPM | ± SD | % inhib. |
| 20 mM | 76 | 9 | (9.99) | 134 | 51 | (9.99) |
| 6.7 mM | 112 | 35 | (9.99) | 4402 | 2242 | (95.3) |
| 2.2 mM | 1995 | — | (97.5) | 43264 | 10237 | (53.7) |
| 740 μM | 61568 | 8943 | (23.6) | 88958 | 2804 | (4.8) |
| 247 μM | 73805 | 13480 | | 86893 | 4332 | |
| MEDIA | 80578 | 8523 | | 93421 | 9086 | |
| PBL | 11658 | 122 | | 50760 | 1581 | |
| EBV | 196 | 35 | | 153 | 62 | |

Viability Testing

In order to insure that the immunosuppressive effect of the succinylacetone derivatives was not being caused by generalized cytotoxicity, the effect of succinylacetone methyl ester, and methyl 4-acetyl-5-oxohexanoate on the viability of peripheral blood lymphocytes in a phytohaemagglutination stimulation assay was determined. Viability was determined using the trypan blue exclusion method well known in the art. Tables 8 and 9 show the results for succinylacetone methyl ester and methyl 4-acetyl-5-oxohexanoate, respectively. The assays were conducted in duplicate wherein peripheral blood lymphocytes were isolated from two separate individuals, and then treated with or without phytohemagglutinin in the presence of various concentrations of the appropriate succinylacetone derivative. Table 8 shows there is little viability at a concentration of about 6.7 mM succinylacetone methyl ester. However, viability is greatly increased, and is nearly 100%, at a concentration ranging between 2.2 mM and 733 μM. These concentrations are those which were shown to be effective in the immunosuppressive assays described above. Surprisingly, methyl 4-acetyl-5-oxohexanoate exhibits no toxicity even at concentrations as high as 20 mM (Table IX).

TABLE VIII

Viability Methyl Ester SA

| Sample* | (−) PHA | | (+) PHA | | (−) PHA | | (+) PHA | |
|---|---|---|---|---|---|---|---|---|
| | Cells/ml | % Via | Cells/ml | % Via | Cells/ml | % Via | Cells/ml | % Via |
| 20 mM | ND | 0 | ND | 0 | ND | 0 | ND | 0 |
| 6.7 mM | 0.15 | 7 | 0.13 | 8 | 0.23 | 4 | 0.24 | 6 |
| 2.2 mM | 0.36 | 94 | 0.3 | 89 | 0.42 | 94 | 0.42 | 93 |
| 733 μM | 0.34 | 96 | 0.4 | 90 | 0.48 | 95 | 0.39 | 94 |
| 244 μM | 0.35 | 100 | 0.38 | 97 | 0.46 | 98 | 0.52 | 96 |
| 81 μM | 0.37 | 100 | 0.4 | 96 | 0.53 | 100 | 0.55 | 98 |
| 27 μM | 0.60 | 100 | 0.37 | 97 | 0.43 | 100 | 0.40 | 94 |
| 9 μM | 0.36 | 100 | 0.32 | 100 | 0.51 | 100 | 0.50 | 100 |
| 3 μM | 0.60 | 100 | 0.48 | 100 | 0.5 | 100 | 0.50 | 100 |
| MEDIA | 0.5 | 100 | 0.52 | 98 | 0.4 | 100 | 0.48 | 100 |

*×10⁶

TABLE IX

PBL Viability Methyl 4-Acetyl-5-Oxohexanoate

| Sample* | (−) PHA | | (+) PHA | | (−) PHA | | (+) PHA | |
|---|---|---|---|---|---|---|---|---|
| | Cells/ml | % Via | Cells/ml | % Via | Cells/ml | % Via | Cells/ml | % Via |
| 20 mM | 0.5 | 100 | 0.49 | 100 | 0.5 | 100 | 0.55 | 100 |
| 6.7 mM | 0.57 | 100 | 0.46 | 100 | 0.6 | 100 | 0.50 | 100 |
| 2.2 mM | 0.57 | 100 | 0.49 | 100 | 0.54 | 100 | 0.50 | 100 |
| 733 μM | 0.37 | 100 | 0.38 | 100 | 0.41 | 100 | 0.40 | 100 |

TABLE IX-continued

| | PBL Viability Methyl 4-Acetyl-5-Oxohexanoate | | | | | | | |
|---|---|---|---|---|---|---|---|---|
| | (−) PHA | | (+) PHA | | (−) PHA | | (+) PHA | |
| Sample* | Cells/ml | % Via | Cells/ml | % Via | Cells/ml | % Via | Cells/ml | % Via |
| 244 µM | 0.40 | 100 | 0.44 | 100 | 0.5 | 100 | 0.54 | 100 |
| 81 µM | 0.42 | 100 | 0.38 | 100 | 0.46 | 100 | 0.40 | 100 |
| 27 µM | 0.44 | 100 | 0.46 | 100 | 0.50 | 100 | 0.50 | 100 |
| 9 µM | 0.55 | 100 | 0.47 | 100 | 0.52 | 100 | 0.50 | 100 |
| 3 µM | 0.39 | 100 | 0.45 | 100 | 0.44 | 100 | 0.40 | 100 |
| MEDIA | 0.44 | 100 | 0.38 | 100 | 0.43 | 100 | 0.48 | 100 |

*×10$^6$

In Vivo Results

The immunosuppressive effects of two of the derivatives of succinylacetone were determined in a rheumatoid arthritis experimental animal model system, and compared to the effects of succinylacetone. The derivatives were succinylacetone methyl ester and methyl 4-acetyl-5-oxohexanoate. The experimental model system was adjuvant induced arthritis in rats, and the protocol is described by J. Holoshitz, et al., Science 219:56 (1983), or by B. Waksman and C. Wennersten, Int. Arch. Allergy Appl. Immunol. 23:129 (1963). Induction of the disease can be caused by a single injection, generally intradermally, of a suspension of killed Mycobacterium tuberculosis in complete Freund's adjuvant (CFA). The route of injection can vary, but in the instant invention rats were injected at the base of the tail with an adjuvant mixture.

The procedure for testing the effects of succinylacetone methyl ester and methyl 4-acetyl-5-oxohexanoate consisted of intradermally injecting killed Mycobacterium tuberculosis in CFA followed by either immediate treatment every other day with the derivatives of subsequent administration starting at 4 or 14 days later. The derivatives were administered intraarticularly into the right paw at concentrations of 325 µg, 150 µg, and 560 µg per kilogram of body weight of succinylacetone, succinylacetone methyl ester, and 4-acetyl-5-oxohexanoate, respectively.

Table 10 shows the effects of succinylacetone methyl ester and methyl 4-acetyl-5-oxohexanoate along with succinylacetone. Experiment I consisted of administering Mycobacterium in CFA and the appropriate compound on the same day, and every other day until day 24. Experiments II and III were similarly performed with the difference that succinylacetone or the derivatives were administered every other day starting at 4 or 14 days respectively, after Mycobacterium/CVA administration until day 24. At the appropriate times, 14, 16, 18, 20 and 22 days after injection of Mycobacterium CFA, an overall arthritis score was obtained as described by J. Holoskitz above. It is apparent that the methyl ester derivative is most effective when it is administered 14 days after induction of the disease, (Exp. III, Table X). Moreover, succinylacetone is also effective when administered 14 days subsequent to injection of Mycobacterium tuberculosis plus CFA. In contrast, 4 acetyl-5-oxohexanoate is apparently most active when administered every other day from day 4 to day 24.

TABLE X

| COMPOUND | | TIME (DAYS) | | | | | | |
|---|---|---|---|---|---|---|---|---|
| | | 14 | 16 | 18 | 20 | 22 | 24 | 26 |
| Succinylacetone | Exp. I | 0.6 ± 1.3 | 0.8 ± 1.8 | 1.4 ± 2.6 | 3 ± 5 | 3.8 ± 5 | 4 ± 3.9 | 5 ± 4.3 |
| | Exp. II | 3.2 ± 3.8 | 3.2 ± 3.8 | 4.8 ± 3.6 | 7 ± 2.3 | 6.2 ± 2.4 | 6 ± 2.7 | 7.8 ± 3 |
| | Exp. III | 2.0 ± 3.9 | 2.0 ± 3.9 | 2.2 ± 2.9 | 2.4 ± 2.9 | 4.0 ± 3.7 | 2.8 ± 2.8 | 3.4 ± 2.7 |
| Succinylacetone | Exp. I | 2.4 ± 2.5 | 2.8 ± 2.4 | 3.4 ± 1.9 | 6.4 ± 3.6 | 6.8 ± 4.0 | 7.2 ± 4.1 | 6.2 ± 3.7 |
| Methyl Ester | Exp. II | 1.6 ± 2.6 | 2 ± 2.8 | 3.2 ± 4.0 | 4.0 ± 4.6 | 4.8 ± 4.1 | 4.8 ± 4.1 | 5.6 ± 4.7 |
| | Exp. III | 1.2 ± 1.8 | 1.4 ± 1.3 | 1.4 ± 2.2 | 4.8 ± 3.8 | 4.4 ± 3.6 | 4.4 ± 3.6 | 3.0 ± 3.3 |
| Methyl 4 Acetyl-5-oxo Hexanoate | Exp. I | 3.2 ± 2.2 | 3.4 ± 2.2 | 5.0 ± 3.2 | 7.0 ± 4.0 | 8.2 ± 4.9 | 7.2 ± 4.2 | 7.2 ± 4.2 |
| | Exp. II | 1.0 ± 1.4 | 2.2 ± 2.5 | 1.8 ± 1.8 | 2.2 ± 2.0 | 5.0 ± 3.5 | 3.4 ± 3.6 | 4.0 ± 3.7 |
| | Exp. III | 2.0 ± 2.0 | 2.4 ± 1.5 | 3.4 ± 2.6 | 5.6 ± 2.7 | 7.4 ± 4.8 | 7.4 ± 5.3 | 7.4 ± 5.3 |

SYNTHESIS

A number of succinylacetone derivatives described herein were produced as follows. For preparation of succinylacetonyl-proline-NH-PEG, an attempt was made first to generate an active ester of succinylacetone. Succinylacetone was dissolved in an aprotic organic solvent, (preferably dimethyl formamide, chloroform, or dichloromethane, among others), and converted to an ester by addition of an equimolar amount of an appropriate condensing agent, such as a carbodiimide, (preferably dicyclohexyl carbodiimide, or 1-ethyl-3-(3-dimethylamino-propyl)-carbodiimide (EDAC)), and a slight molar excess of an appropriate ester forming alcohol, (preferably p-nitrophenol, 4-hydroxyl-3-nitro-benzene sulfonate, or N-hydroxysuccinimide, among others). It is expected that this reaction would produce an active ester from the alcohol and succinylacetone. However, subsequent experiments revealed that an enol lactone is, indeed, an intermediate in the reaction, and this was confirmed by subsequent NMR analyses of succinylacetone reacted with carbodiimide in the absence of an alcohol. Enol-lactone, in turn, reacts with both primary and secondary amines to produce the desired amides. Concomitant with the formation of the enol-lactone is the formation of ureas from the carbodiimide.

When succinylacetone is treated as described-above with a secondary amine such as proline, the product formed is succinylacetonyl-proline. Succinylacetonyl-proline can be converted to succinylacetonyl-proline-NH-PEG by combining it with a condensing agent, in the presence of a suitable ester forming alcohol to form an active ester of the carboxylic acid group of proline. The preferred alcohol is p-nitrophenol, although other alcohols such as, for example, N-hydroxysuccinimide, 4-hydroxy-3-nitro-benzenesulfonate, among others may be used. The final step in this reaction sequence is to react the succinylacetonyl-prolyl-nitrophenyl active ester with PEG-NH$_2$ which results in the desired product, succinylacetonyl-proline-NH-PEG.

The succinylacetone active esters, or other activated species, formed in the step described above are also reactive with primary amines, which thus affords a synthetic route towards realizing succinylacetone PEG, which was employed as a control in a number of the experiments. Succinylacetonyl-NH-PEG is realized by combining succinylacetone active species, probably the enol-lactone, or other activated species with PEG-NH$_2$ which produces succinylacetonyl-NH-PEG.

Succinylacetonyl-Proline-NH-PEG

Succinylacetonyl-Proline

In more detail, succinylacetonyl-proline-NH-PEG was synthesized by first generating succinylacetonyl-proline. This consisted of dissolving 1 gm of succinylacetone (6.3 mmole) and 1.6 gm (6.6 mmole) of 1-hydroxyl-2-nitro-benzene-4-sulfonic acid in 10 ml dimethyl formamide. Next a suitable condensing agent was added, particularly useful is dicyclohexylcarbodiimide. About 1.6 g of dicyclohexylcarbodiimide (6.3 mmole) was added to the mixture. After the reaction was stirred at room temperature for a short time (10 minutes), dicyclohexylurea began to precipitate. Dicyclohexylurea was removed from the reaction mixture by filtering, followed by adding the filtrate to a dimethyl formamide solution containing 0.74 g proline (6.3 mmole). The combined solutions were stirred overnight.

The reaction was diluted with an equal volume of water, and extracted ten times with 10 ml of ethyl acetate. The combined organic extracts were dried over MgSO$_4$, filtered to remove MgSO$_4$ hydrate, and concentrated on a rotary evaporator to produce a thick slurry. Succinylacetone was separated from succinylacetonyl-proline using a 4 mm Chromatotron spinning plate silica gel chromatogram equilibrated with a solvent consisting of chloroform:acetic acid in the ratio of 90:10. Succinylacetone eluted at the solvent front. Succinylacetonyl-proline eluted with a more polar solvent consisting of chloroform:acetic acid:methanol in the ratio of 90:10:3. Those fractions containing succinylacetonyl-proline were pooled, concentrated with a rotary evaporator and the remaining acetic acid solution diluted with water, followed by quick freezing and lyophilization. The final product was a yellow oil.

In a thin layer chromatography plate developed in 90:10 chloroform:acetic acid succinylacetone showed an $R_f$ of 0.78 while the product succinylacetonyl-proline has an $R_f$ of 0.23, and proline remains at the origin.

Succinylacetonyl-proline-NH-PEG

Succinylacetonyl-proline was converted to succinylacetonyl-proline-NH-PEG by adding succinylacetonyl-proline to a condensing agent in the presence of p-nitrophenol in chloroform. The reaction was carried out in 10 ml of chloroform by adding 0.55 g (4.0 mmole) of p-nitrophenol to 0.64 g (3.9 mmole) of succinylacetone-proline. Next, 0.80 g (3.3 mmole) of the condensing agent, dicyclohexylcarbodiimide was added. The latter was dissolved in 2 ml chloroform, and added slowly to the mixture with stirring. Within 10 minutes, a white precipitate of dicyclohexylurea formed, and a spectrophotometric determination [L. Aldwin and D. E. Nitecki, 1987, *Anal. Biochem.*, 164:494–501] of the amount of ester present at that time indicated that there was approximately 61.5% ester present. A similar determination two hours later revealed no change in the amount of ester formed. Dicyclohexylurea was removed by filtering the solution, followed by the addition of 0.45 g (1.1 mmole) PEG-4000-NH$_2$ to the filtrate. The reaction mixture was allowed to stir at room temperature overnight. The product, succinylacetonyl-proline-NH-PEG was purified as follows.

Figure 3:
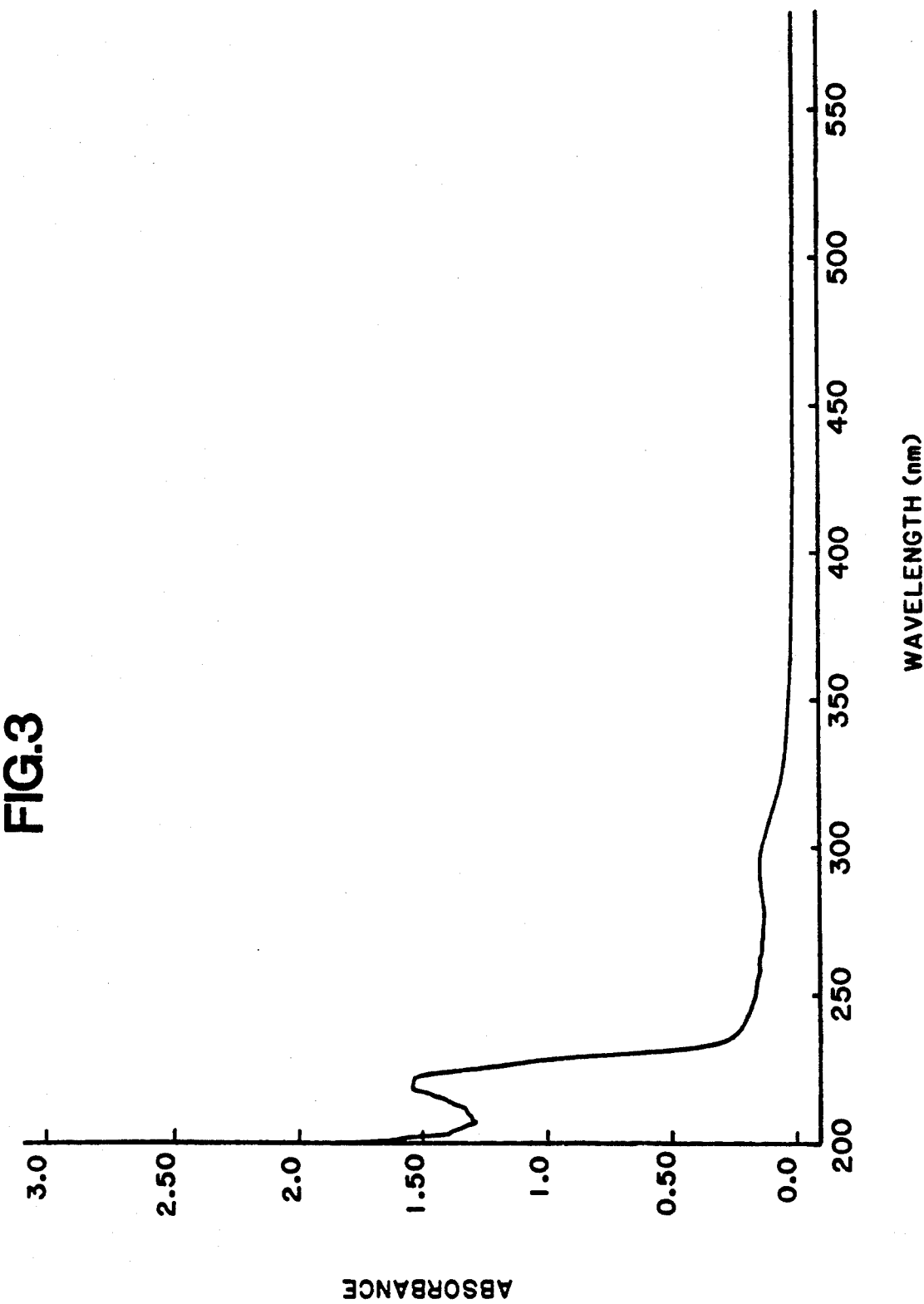
FIG. 3 shows the absorbance spectra of fractions 15-34 from the Sephadex G-50 column.
Figure 4:
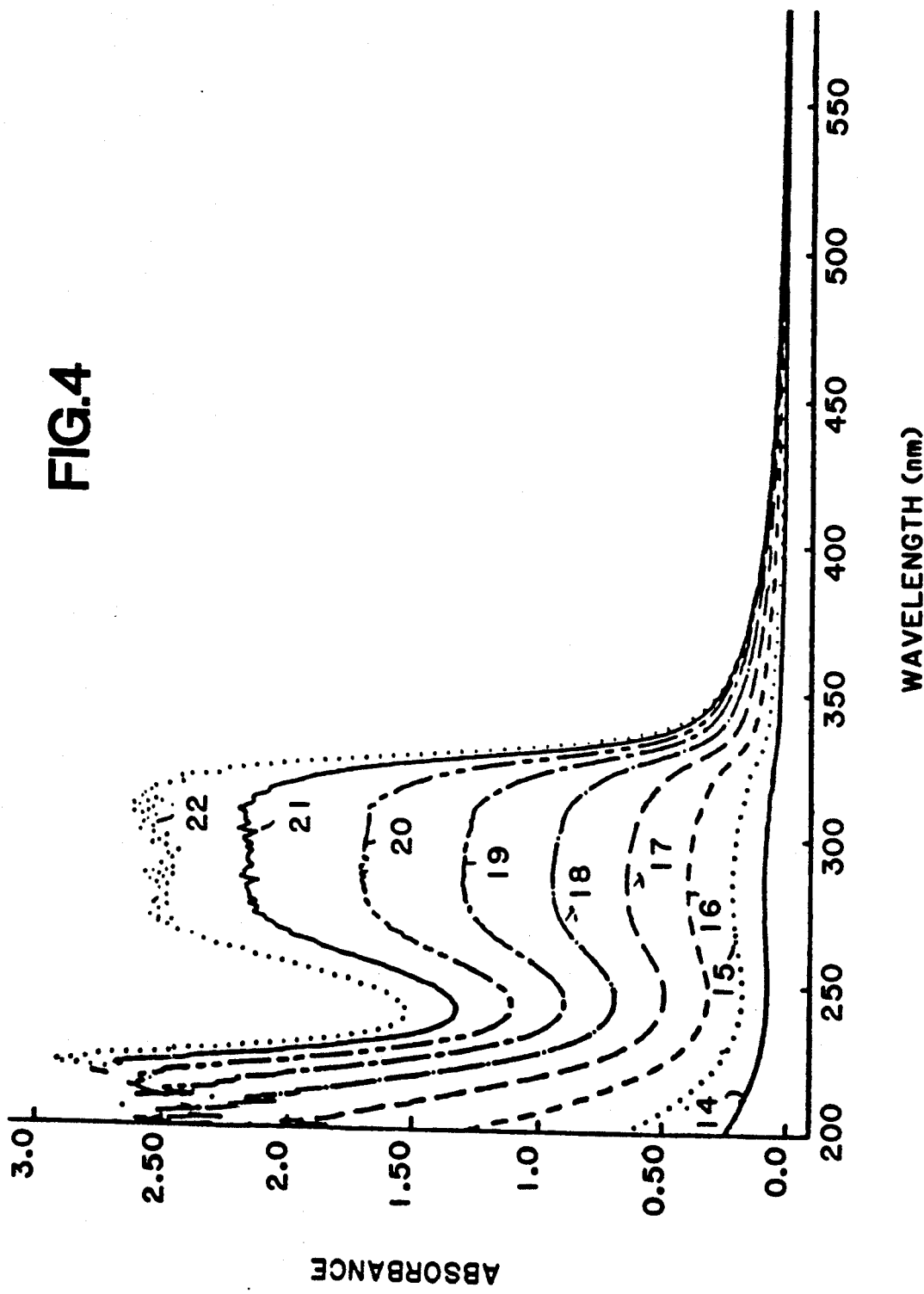
FIG. 4 shows the absorbance spectrum of PEG-4000 $NH_2$.

The reaction mixture had a granular appearance, and therefore was filtered, followed by removal of the organic solvent with a rotary evaporator. This left a thick oil in the rotary evaporator flask which was not completely soluble in water. It was extracted three times with ethyl ether, to remove impurities which were not water soluble. PEG is completely insoluble in ethyl ether, and therefore succinylacetonyl-proline-PEG was expected to remain in the aqueous phase. The aqueous phase was applied to a G-50 Sephadex sizing column (3 cm diameter×41 cm high) that had previously been equilibrated with distilled water. The column was washed with distilled water and 4 ml fractions collected and monitored spectrophotometrically to produce the elution profile shown in FIG. 2. This chromatographic step primarily separates small molecular weight molecules such as succinylacetonyl-proline from larger ones such that PEG-4000-NH$_2$ and succinylacetonyl-proline-NH-PEG co-elute. Spectrophotometric analysis of fractions 16–34 from the Sephadex G-50 column revealed that this material absorbs between 250–340 nm. This is in contrast to PEG-4000-NH$_2$ which absorbs in the range of about 210–225 nm. These results are shown in FIGS. 3 and 4. FIG. 3 shows the spectrum of PEG-4000-NH$_2$, while FIG. 4 shows the spectra of some of the Sephadex G-50 fractions.

Fractions 15–34 were pooled and lyophilized to a white powder. Thin layer chromatography plates developed in 90:10 chloroform:acetic acid indicated that most of the ninhydrin reacting compound remained at the origin. No succinylacetone was detectable on the plate, but trace amounts of succinylacetonyl-proline could be seen. This method was used to produce the compounds for the bioassays shown in Table 1. The mixture was later repurified over a G-50 Sephadex column so that no trace of succinylacetone-proline could be detected on TLC plates. The purer succinylacetone-proline-NH-PEG-4000 was used in the bioassays shown in Table 2.

Succinylacetonyl-NH-PEG

Approximately 0.158 grams (1.0 mMole) of succinylacetone was combined with 1.0 gram of PEG-NH$_2$ (molecular weight 10K) in 10 ml chloroform. Next 0.206 grams of dicyclohexylcarbodiimide was added in a small amount of chloroform. The reaction was allowed to proceed at room temperature overnight and was shielded from exposure to light. The major by-product of the reaction, dicyclohexylurea, was removed by filtration, and the slightly yellow filtrate concentrated by rotary evaporation. The remaining oil was dissolved in H$_2$O and dialyzed against dilute acetic acid, and subsequently water. After three changes of dilute acetic acid and three changes of water, the contents of the dialysis bag were lyophilized. The white powder was redissolved in distilled water and was chromatographed over a gel filtration column, Sephadex G-50 (available from Pharmacia Corp.), to remove small molecular weight impurities. Fractions containing succinylacetonyl-NH-PEG were identified spectrophotometrically, and shown to contain succinylacetonyl-NH-PEG by thin layer chromatography.

Succinylacetone Methyl Ester

Succinylacetone methyl ester, methyl 4-6-dioxoheptanoate, was synthesized as described by A. R. Battersby, et al., *J. C. S. Perkin I*, 1981:2786-2792.

Glutarylacetone Methyl Ester

Glutarylacetone methyl ester, (methyl 5,7-dioxohexanoate), was synthesized by reacting a magnesium complex of t-butyl acetoacetate with methyl 4-(chloroformyl) butyrate. The magnesium complex of t-butyl acetoacetate, in turn, was synthesized as described by Battersby, 1981, *J. Chem Soc.*, Perkin Transactions I, p. 2786-2799. Briefly, methanol (250 mL) was added to a mixture of magnesium shavings (15.91 gm; 654.5 mmole) and 0.5 mL of carbon tetrachloride. The mixture began to reflux as the metal dissolved and a cold water bath was used to control the reaction. After the metal had completely dissolved in the alcohol, and the mixture had cooled, t-butyl acetoacetate (106.7 mL; 101.8 gm; 664.2 mmole) was added dropwise over ten minutes. The mixture was refluxed for one hour, cooled, and filtered. The magnesium complex of t-butyl acetoacetate was collected, washed with cold methanol and dried under vacuum.

To a suspension of the magnesium complex of t-butyl acetoacetate (75 gm; 353 mmole) in 125 mL of ether was added methyl 4-(chloroformyl) butyrate (54 mL; 64.31 gm; 391 mmole). The addition was made dropwise, with stirring under a reflux condenser. After the addition was complete, the mixture was refluxed for thirty minutes and allowed to cool. To the mixture was added 125 mL of 1.8 M sulfuric acid and the two-phase mixture transferred to a one liter separatory funnel. The aqueous layer was extracted with ether (3×100 mL) and the combined ether extracts were washed with brine (4×50 mL). The ether was evaporated and to the residue was added 300 mg of p-toluenesulfonic acid monohydrate. The mixture was heated to 170° C. and evolution of gas monitored with a bubbler. When gas evolution had subsided, the dark mixture was allowed to cool and 250 mL of ether was added. The solution was transferred to a one liter separator funnel and extracted with ice-cold 2 M sodium hydroxide (100, 50, 25 and 25 mL). The extracts were run directly into ice-cold 1.8 M sulfuric acid (250 mL). The acidic suspension was extracted with methylene chloride (3×150 mL). The organic extracts were pooled and washed with 5% sodium bicarbonate (2×50 mL) and brine (2×50 mL), dried over sodium sulfate, filtered and the solvent removed under reduced pressure to yield 40 gm of dark syrup. This was taken up in 200 mL methylene chloride and adsorbed onto 60 gm silica gel by evaporation of the solvent and fractionated on a 600 mL column of silica gel by flash chromatography using ethyl acetate:hexane (1:4) as eluant. Fractions containing the product were pooled and concentrated to a pale yellow oil weighing 33.08 gm. The $R_f$ value (silica gel; ethyl acetate:hexane 1:4) was 0.31, which is consistent with the product being glutarylacetone methyl ester as assessed by elemental analysis and the NMR spectrum of the product.

Adipoylacetone Methyl Ester

Adipoylacetone methyl ester (methyl 6,8-dioxononanoate) was generated by reacting the magnesium complex of t-butyl acetonacetate with methyl adipoyl chloride. t-Butyl acetoacetate magnesium complex was synthesized as described above, and to a suspension of the complex (10.6 gm; 50 mmole) in 25 mL of ether was added methyl adipoyl chloride (9.83 gm; 55 mmole). The addition was made dropwise with stirring under a reflux condenser. After the addition was complete, the mixture was refluxed for thirty minutes and allowed to cool. To the mixture was added 25 mL of 1.8 M sulfuric acid and the two-phase mixture transferred to a 125 mL separatory funnel. The aqueous layer was extracted with ether (3×25 mL) and the combined ether extracts were washed with brine (4×10 mL). The ether was evaporated and to the residue was added 100 mg of p-toluene sulfonic acid monohydrate. The mixture was heated to 170 degrees and evolution of gas monitored with a bubbler. When gas evolution had subsided, the dark mixture was allowed to cool and 50 mL of ether was added. The solution was transferred to a one liter separatory funnel and extracted with ice-cold 2 M sodium hydroxide (20, 10, 5 and 5 mL). The extracts were run directly into ice-cold 1.8 M sulfuric acid (25 mL). The acidic suspension was extracted with methylene chloride (3×30 mL). The organic extracts were pooled and washed with 5% sodium bicarbonate (2×10 mL) and brine (2×10 mL), dried over sodium sulfate, filtered and the solvent removed under reduced pressure to yield 7.05 gm of dark syrup. This was taken up in 50 mL methylene chloride and adsorbed onto 15 gm silica gel and fractionated on a column of silica gel by flash chromatography using ethyl acetate:hexane (1:4) as eluant. Fractions containing the product as determined by TLC were pooled and concentrated to a pale yellow oil weighing 5.39 gm. The $R_f$ value (silica gel; ethyl acetate:hexane 1:4) was 0.30. Elemental analysis and NMR spectrum of the product was consistent with the expected material.

Glutarylacetone

Glutarylacetone, 5,7-dioxo octanoic acid), was generated from glutarylacetone methyl ester by hydrolysis. Briefly, glutarylacetone methyl ester (1.0 g) was hydrolyzed in 10 ml of 4.0 M HCl at 90° for 30 minutes. The solution was cooled and extracted with four 25 ml portions of methylene chloride. After drying over magnesium sulfate and evaporation of the solvent, the residue was recrystallized from ether-hexane to give 0.3 g of crystalline 5,7-dioxo octanoic acid.

Additional Synthesis

In addition to the above compounds, it will be appreciated that other succinylacetone analogs or derivatives may be made according to the following proposed synthetic schemes.

Succinyl Trifluoroacetone Methyl Ester (Methyl 7,7,7-trifluoro 4,6-dioxoheptanoic acid)

Methanol (250 mL) is added to magnesium shavings (15.91 gm; 654.5 mmole) containing 0.5 mL of carbon tetrachloride. The mixture refluxes as the metal dissolved, and a cold water bath is used to control the reaction. After the mixture has completely dissolved and cooled, t-butyl 3-oxo-4,4,4-trifluorobutanoate (140.9 gm; 664.1 mmole) is added dropwise over ten minutes. This mixture is refluxed for one hour, cooled, filtered and the resulting solid collected and washed with cold methanol and dried under vacuum.

The magnesium complex of t-butyl 3-oxo-4,4,4-trifluorobutanoate (266.5 gm; 635 mmole) is suspended in 250 ml of anhydrous ether in a three-neck one liter round bottom flask and carbomethoxypropionyl chloride (100 gm: 664 mmole) added dropwise over fifteen minutes while the mixture is stirred from overhead. The dropping funnel is removed and the mixture refluxed for thirty minutes. The mixture is cooled and 250 ml of 2 N aqueous sulfuric acid slowly added. The mixture is transferred to a one liter separator funnel and the layers separated. The aqueous layer is extracted with ether (2×150 ml) and the combined ether extracts washed with water (4×100 ml). The ether is evaporated and to the residual red oil is added 800 mg of toluene sulfonic acid monohydrate. The mixture is heated in an oil bath (with reflux condenser) to 175 degrees until evolution of gas ceases. The mixture is cooled and taken up in 500 ml of ether. The ether extracted with ice-cold 2 M aqueous sodium hydroxide (175, 90 50, and 35 ml), and the extracts run from the separatory funnel directly into 250 ml of ice-cold 1.8 M aqueous sulfuric acid. The acidic suspension is extracted with methylene chloride (3×150 ml) and the combined organic extracts were washed with 5% aqueous sodium bicarbonate (2×100 ml) and brine (100 ml). The residue after evaporation of the methylene chloride may be purified by silica gel flash column chromatography using as eluant chloroform:methanol 97:3.

Succinyl Trifluoroacetone From the Methyl Ester

The methyl ester (2.63 gms; 11.62 mmole) is suspended in 18 mL water and 2 mL of conc. HCl added. The mixture is heated with stirring at 50 degrees for two hours or until all the material dissolved. The solvent is removed under reduced pressure (aspirator at 50 degrees) and the residue taken up in 18 mL water and 2 mL of conc. HCl added. Again, the solution is heated at 50 degrees for two hours at which time TLC (methylene chloride:methanol 97:3) should show no ester remained (UV and ferric chloride spray reagent; 2.7% w/v in 2 N HCl). The solvent is once again removed underreduced pressure (water pump, 50 degrees) and 20 mL water added. The water is removed under reduced pressure (water pump, 50 degrees) and residual water removed by azeotroping with 50 mL of toluene. To the residue is added 50 mL ether and the solvent removed on the roto-vap. Finally, the residue is taken up in 10 mL of hot ether and filtered. Addition of four mL of hexane to the filtrate initiates crystallization and the flask is chilled. Crystals may be removed by filtration and dried.

Methyl 2(2,4-Dioxobutyl) Benzoate

The magnesium complex of t-butyl acetoacetate (135 gm; 635 mmole) is suspended in 250 ml of anhydrous ether in a three-neck one liter round bottom flask and mono-methyl phthaloyl chloride (192 gm: 664 mmole) is added over fifteen minutes while the mixture is stirred from overhead. The dropping funnel is removed and the mixture refluxed for thirty minutes. The mixture is cooled and 250 ml of 2 N aqueous sulfuric acid slowly added. The mixture is transferred to a one liter separatory funnel and the layers separated. The aqueous layer is extracted with ether (2×150 ml) and the combined ether extracts washed with water (4×100 ml). The ether is evaporated and to the residual red oil is added 800 mg of toluene sulfonic acid monohydrate. The mixture is heated in an oil bath (with reflux condenser) to 175 degrees until evolution of gas has ceased. The mixture is cooled and taken up in 500 ml of ether. The ether is extracted with ice-cold 2 M aqueous sodium hydroxide (175, 90, 50, and 35 ml), and the extracts run from the separatory funnel directly into 250 ml of ice-cold 1.8 M aqueous sulfuric acid. The acidic suspension is extracted with methylene chloride (3×150 ml) and the combined organic extracts washed with 5% aqueous sodium bicarbonate (2×100 ml) and brine (100 ml). The residue after evaporation of the methylene chloride may be purified by silica gel flash column chromatography to yield the product.

2(2,4-Dioxobutyl) Benzoate From The Methyl Ester

The methyl ester (2.56 gms; 11.62 mmole) is suspended in 18 mL water and 2 mL of conc. HCl added. The mixture is heated with stirring at 50 degrees for two hours (all material had dissolved). The solvent is removed under reduced pressure (aspirator at 50 degrees) and the residue taken up in 18 mL water and 2 mL of conc. HCl added. Again, the solution is heated at 50 degrees for two hours at which time TLC (methylene chloride:methanol 97:3) will show no ester remaining. (UV and ferric chloride spray reagent; 2.7% w/v in 2 N HCl). The solvent is once again removed under reduced pressure (water pump, 50 degrees) and 20 mL water added. The water is removed under reduced pressure (water pump, 50 degrees) and residual water removed by azeotroping with 50 mL of toluene. To the residue is added 50 mL ether and the solvent removed on the roto-vap. Finally, the residue is taken up in 10 mL of hot ether and filtered. Addition of four mL of hexane to the filtrate initiates crystallization and the flask is chilled. Crystals may be removed by filtration and dried.

3,5-Dioxohexylcyanide

The magnesium complex of t-butyl acetoacetate (135 gm; 635 mmole) is suspended in 250 ml of anhydrous ether in a three-neck one liter round bottom flask and beta-cyano propionyl chloride (78.05 gm; 664 mmole) added dropwise over fifteen minutes while the mixture is stirred from overhead. The dropping funnel is removed and the mixture refluxed for thirty minutes. The mixture is cooled and 250 ml of 2 N aqueous sulfuric acid is slowly added. The mixture is transferred to a one liter separatory funnel and the layers separated. The aqueous layer is extracted with ether (2×150 ml) and the combined ether extracts washed with water (4×100 ml). The ether is evaporated and to the residual red oil is added 800 mg of toluene sulfonic acid monohydrate. The mixture is heated in an oil bath (with reflux condenser) to 175 degrees until evolution of gas has ceased. The mixture is cooled and taken up in 500 ml of ether. The ether is extracted with ice-cold 2 M aqueous sodium hydroxide (175, 90, 50, and 35 ml). The extracts were run from the separatory funnel directly into 250 ml of ice-cold 1.8 M aqueous sulfuric acid. The acidic suspension is extracted with methylene chloride (3×150 ml) and the combined organic extracts washed with 5% aqueous sodium bicarbonate (2×100 ml) and brine (100 ml). The residue after evaporation of the methylene chloride may be purified by silica gel flash column chromatography using ethyl acetate:hexane 1:4 as eluant.

5-(3,5-Dioxohexyl) Tetrazole

A mixture of the 3,5-dioxohexylcyanide (2.78 gm; 20 mmole), lithium azide (1.08 gm; 22 mmole) and sulfuric acid (one drop) in 10 ml dry dimethylformamide is heated to 100–120 degrees. Progress of the reaction may be checked by TLC (silica gel; chloroform:methanol 97:3). When no starting material remains, the reaction is cooled and 20 ml of water added. The reaction is taken to dryness under reduced pressure and the residue fractionated by silica gel flash column chromatography using methylene chloride:glac. acetic acid; methanol 100:3:3 as eluant. Fractions containing the product may be pooled and concentrated.

Beta-Keto t-Butyldimethylsilyl Enol Ethers Of SA Methyl Ester

To a solution of succinyl acetone methyl ester (3.44 gm; 20 mmole) in 50 ml THF is added a 50% dispersion of sodium hydride in mineral oil (960 mg; 20 mmole) and the mixture stirred until gas evolution ceases. To the mixture of enolates is added a solution of t-butyl dimethylsilyl chloride (3.32 gm; 22 mmole) in 50 ml THF dropwise with stirring. Sodium chloride is removed by filtration and the residue fractionated by silica gel flash chromatography using ethyl acetate:hexane as eluant.

Beta-Keto Isopropyl Enol Esters Of SA Methyl Ester

To each of the purified t-butylmethylsilyl enol ethers of SA methyl ester (2.87 gm; 10 mmole) in THF cooled to $-78$ degrees is added tetrabutylammonium fluoride in THF (11 mmole). After thirty minutes at $-78$, 2-iodopropane (1.87 gm; 11 mmole) is added to the mixture and the reaction allowed to slowly reach room temperature. The solvent is removed under reduced pressure and the residue purified by silica gel flash chromatography to yield the isopropyl enol ethers.

Beta-Hydroxy Keto Derivatives Of SA Methyl Ester

To a solution of each of the t-butyldimethylsilyl enol ethers of SA methyl ester (2.87 gm; 10 mmole) in 50 ml of isopropanol at $-20$ degrees is added sodium borohydride (420 mg; 11 mmole). When no starting material remains tetrabutylammonium fluoride (2.88 gm; 11 mmole) is added and reaction progress followed by TLC. Work-up by silica gel column chromatography should yield the hydroxy keto derivatives.

It will be appreciated by those skilled in the art that an alternative approach to these compounds would be via catalytic hydrogenation of the enol double bond in the t-butyldimethylsilyl enol ether of SA methyl ester followed by fluoride mediated silyl ether cleavage to yield the desired hydroxy keto derivatives.

Methyl 4,6,8-Trioxo Nonanoate

To the dilithium salt of 2,4-pentanedione (2.24 gm; 20 mmole) in 50 ml dry THF is added carbomethoxypropionyl chloride (3.31 gm; 22 mmole) dropwise with stirring at zero degrees. When TLC shows no starting material remaining, the solvent is removed under reduced pressure and the residue fractionated by flash chromatography on silica gel using ethyl acetate:hexane as eluant.

It will be apparent to those skilled in the art that the above-described methyl esters could be converted to the corresponding free acids by appropriate methods.

Having described what applicants believe is their invention, it is important to note that it will be apparent to those skilled in the art that there are many possible substitutions for the specific materials and methods shown above. It will be understood that these substitutions are intended to come within the scope of the following claim.

What is claimed is:

1. A method suppressing the effectiveness of a patient's immune system comprising: administering to the patient a therapeutically effective amount of an analogue or derivative of succinylacetone, wherein said analogue or derivative of succinylacetone comprises the formula $$R-\underset{R'}{\overset{O}{\|}}\underset{R''}{\overset{}{C}}-(CH_2)_n R'''$$

wherein n = 1-6

$R = CH_3, CF_3, -CO_2R^{II}, -\overset{O}{\overset{\|}{C}}H, \text{ or } -\overset{O}{\overset{\|}{C}}CH_3$ $R^I, R^{II} = H, F, CH_3, \text{ or } CH_2CH_2\overset{O}{\overset{\|}{C}}OR^{IV}$ $R^{III} = -\overset{O}{\overset{\|}{P}}(OR^{IV})_2$ $R^{IV} = H$, or alkyl.

2. The method as described in claim 1, wherein n=2-6.

3. A method of suppressing the effectiveness of a patient's immune system comprising: administering to a patient a therapeutically effective amount of a succinylacetonyl-proline-PEG or succinylacetonyl-NH-PEG analogue or derivative wherein said analogue or derivative comprises the formula:

$$R-\underset{R'}{\overset{O}{\|}}\underset{R''}{\overset{}{C}}-(CH_2)_n R'''-R^V$$

wherein n = 1-6

$R = CH_3, CF_3, -CO_2R^{II}, -CHO \text{ or } -COCH_3$ $R^I, R^{II} = H, F, CH_3, \text{ or } CH_2CO_2R^{II}$ $R^{III} = -\overset{O}{\overset{\|}{P}}(OR^{IV})_2$ $R^{IV} = H$ or alkyl $R^V = $ -proline-PEG or $-$NH-PEG.

4. The method of claim 3, wherein said effective amount of said analogue or derivative of succinylacetone is about 18 micrograms-800 mg/Kg body weight.

5. The method of claim 4, wherein said succinylacetone analogue or derivative is administered with a pharmaceutically acceptable excipient.

6. The method of claim 5, wherein said disease is an autoimmune disease.

7. The method of claim 6, wherein said disease is the rejection of organ or tissue transplants.

8. The method of claim 5, wherein said disease is a graft versus host disease.

9. Immunosuppressive compositions useful for treating diseases comprising an analogue or derivative of succinylacetone, wherein said analogue or derivative of succinylacetone comprises the formula:

$$R-\underset{R'}{\overset{O}{\|}}\underset{R''}{\overset{}{C}}-(CH_2)_n R'''$$

wherein n = 1-6

-continued

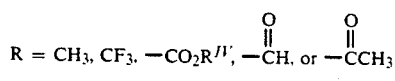

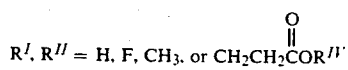

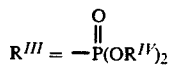

$R^{IV}$ = H, or alkyl.

10. Immunosuppressive compositions as described in claim 9, wherein n=2–6.

11. Immunosuppressive compositions useful for treating diseases comprising a succinylacetonyl-proline-PEG or succinylacetonyl-NH-PEG analogue or derivative wherein said analogue or derivative comprises the formula:

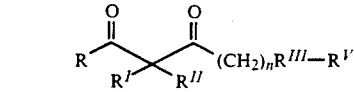

wherein n = 1–6

R = $CH_3$, $CF_3$, $-CO_2R^{IV}$, $-CHO$ or $-COCH_3$ $R^I$, $R^{II}$ = H, F, $CH_3$, or $CH_2CO_2R^{IV}$

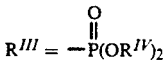

$R^{IV}$ = H or alkyl $R^V$ = -proline-PEG or $-NH$-PEG.

12. Immunosuppressive compositions as described in claim 11 further including a physiologically acceptable excipient.

* * * * *